Dec. 8, 1970 A. WIEBE Plant Pat. 3,009
PEACH TREE
Filed Aug. 30, 1968
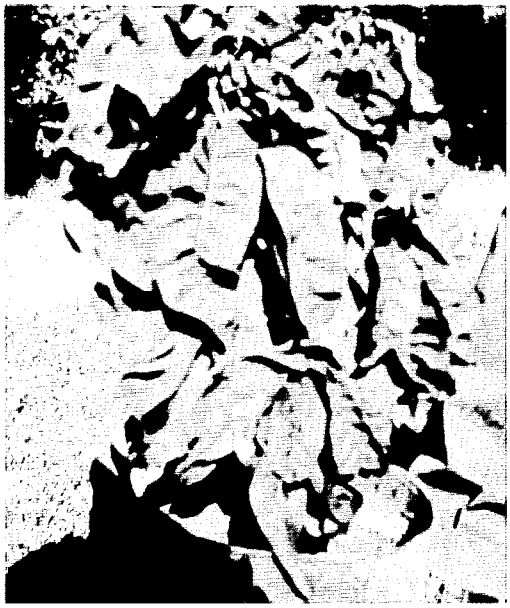
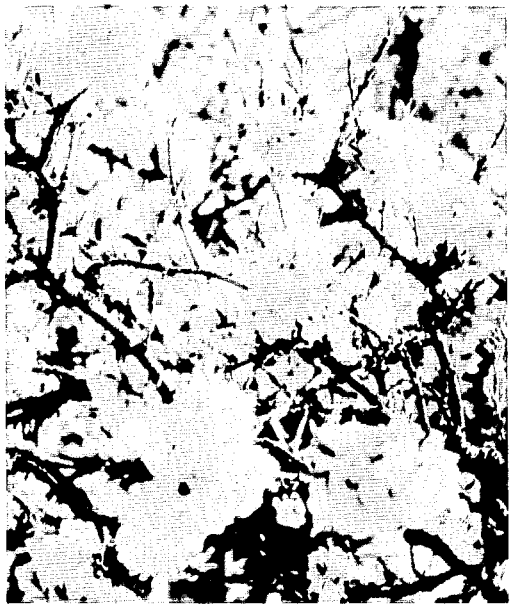
INVENTOR
ARTHUR WIEBE
BY
Fryer, Tjensvold, Feix,
Phillips & Lempio
ATTORNEYS

United States Patent Office

Plant Pat. 3,009
Patented Dec. 8, 1970

3,009
PEACH TREE

Arthur Wiebe, 1174 Vallombrosa Ave., Chico, Calif. 95926

Filed Aug. 30, 1968, Ser. No. 756,692
Int. Cl. A01h *5/03*
U.S. Cl. Plt.—42 1 Claim

This discovery relates to a new and distinct variety of peach tree which is a chance seedling. This chance seedling was found among approximately twenty-five thousand seedlings of Flory Dwarf peach trees grown for the wholesale market. This planting was grown in Chico, Butte County, California. This new plant, which is a small compact dwarf ornamental flowering and fruiting peach tree, has been asexually reproduced at the greenhouse of Vallombrosa Gardens in Chico, Butte County California.

A plant of the new variety is pictured in the accompanying drawing which also shows details of the leaf structure and the flower.

Although this new plant is a chance seedling of the Flory Dwarf peach tree it differs strikingly in the large width, great length and ruffled characteristic of the leaf. Also the growing habit of the new plant is considerably taller and narrower than that of the Flory Dwarf peach tree. At two years the new plant measured 31″ high and 15″ wide compared to a Flory Dwarf which measured 19″ high and 21″ wide.

This new plant grows more erect than the Flory Dwarf which has a tendency to spread out horizontally. The blossoms of the new plant are large double rose red flowers the same as found in the parent Flory Dwarf plant. It blossoms almost as heavily as the Flory Dwarf. The blossoming characteristics of the new plant have an advantage over the parent Flory Dwarf because the blossoms are fewer and less clustered. The Flory Dwarf sometimes blossoms so heavily that the blossoms spoil on the first rain.

The fruit of this new plant is rather large, freestone and almost identical to that produced by the Flory Dwarf. The Flory Dwarf and the new plant produce a white fleshed freestone fruit which is quite delicious to the taste. The fruit has a red blush on its cheek. The fruit of this plant is of at least equal quality to that produced by the Flory Dwarf. The fruit is produced in small clusters and consequently the fruit produced is large.

The leaves of the new plant invention are one of its most striking characteristics. The leaf of this new plant is much longer and wider than that found on any other member of the peach tree family. Leaves of the new plant measure 9″ long and 2½″ wide. The leaf is green and is further characterized by its puffed and fluffy or ruffled appearance which appearance is much like the flower of the Giants of California petunia.

In fact, the leaves are so puffy or fluffy that upon a casual glance it would appear that the leaves are double. Only further inspection reveals that they are in fact individual leaves. The leaf of this new plant is one of its most striking features especially when compared with the Flory Dwarf leaf which is quite narrow and possesses none of the fluffiness that is characteristic of the leaf of the new plant.

The abundancy, size, ruffled and fluffy shape of the leaves tend to give the overall plant a very ornamental and whorled appearance.

Much like the Flory Dwarf the new plant is quite hardy and will thrive well in any locality where other peach trees can be grown. This new variety of plant is planted during the dormant season and will bear fruit the third year after planting.

The varietal characteristics of this new plant, described below in detail, were observed during the growing season of the year 1967. Observations were made in the Chico area of California which has hot summers and relatively cold winters.

Plant: Dwarf, upright, tending to be narrow.

Leaves: Very large, green, wide, ruffled, fluffy and long. The leaves are noticeably pliable and have a glossy surface. The leaves by their abundancy, size, ruffled and fluffy shape tend to give the overall plant a whorled look which is very ornamental and pleasing to the eye.

Flowers: Large, average diameter 1¼″, similar to a conventional flowering peach, rose red in color and heavily doubled.

Fruit: The fruit is very similar but larger than that produced by the Flory Dwarf, white fleshed, freestone with a red cheek. It has a nice pleasing flavor.

*Size.*—Average axial diameter: 2½″; average transverse diameter: 1¾″.

I claim:

1. A new and distinct variety of peach tree, substantially as illustrated and described, characteristized by its large green fluffy and ruffled leaf.

No references cited.

ROBERT E. BAGWELL, Primary Examiner